United States Patent [19]

Brunet

[11] Patent Number: 4,553,962
[45] Date of Patent: Nov. 19, 1985

[54] MEDICAL SYRINGE

[76] Inventor: Jean-Louis Brunet, 14, rue Victor Hugo, 69002 Lyon, France

[21] Appl. No.: 570,772

[22] Filed: Jan. 16, 1984

[30] Foreign Application Priority Data

Jan. 17, 1983 [FR] France ............... 83 00891

[51] Int. Cl.⁴ .............................................. A61M 5/00
[52] U.S. Cl. ..................................... 604/198; 604/232
[58] Field of Search ............... 604/198, 197, 196, 195, 604/194, 232

[56] References Cited

U.S. PATENT DOCUMENTS

| | | | |
|---|---|---|---|
| 3,368,558 | 2/1968 | Sarnoff et al. | 604/198 |
| 3,735,761 | 5/1973 | Hurschman et al. | 604/196 |
| 3,820,542 | 6/1974 | Hurschman | 604/196 |
| 4,258,713 | 3/1981 | Wardlaw | 604/198 |

Primary Examiner—John D. Yasko
Attorney, Agent, or Firm—Karl F. Ross; Herbert Dubno

[57] ABSTRACT

A medical syringe of the type in which an ampule and needle are received in the syringe barrel and a plunger is triggered to drive the needle from the barrel has an ampule whose body is composed of one material, preferably glass, while the needle is sealed and guided by a disk or plug of a different material.

2 Claims, 12 Drawing Figures

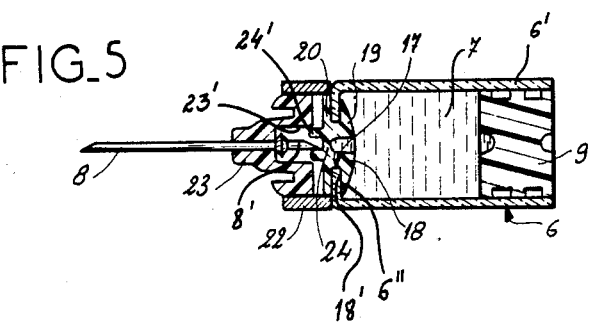
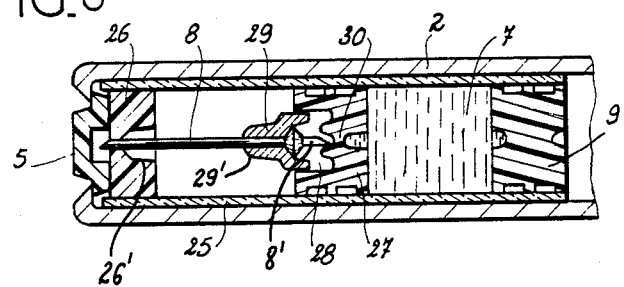
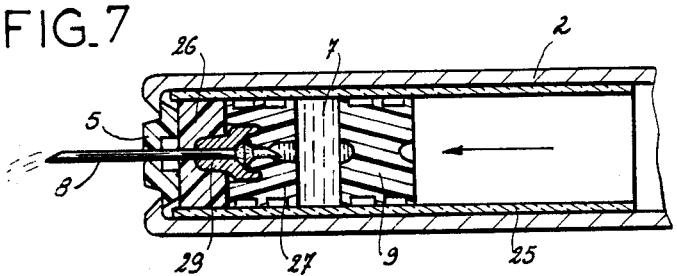
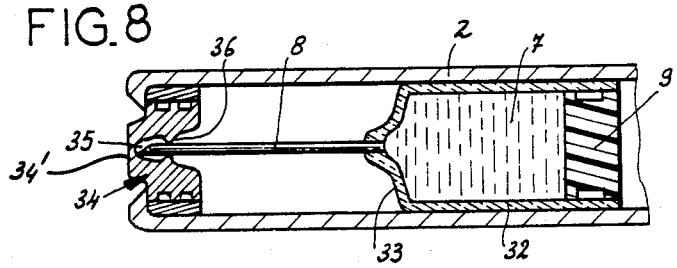

MEDICAL SYRINGE

FIELD OF THE INVENTION

My present invention relates to a medical syringe and, more particularly, to an automatic syringe of the type which allows administration of a medicament through the epidermis of a patient even by an unskilled individual. More particularly, the syringe or the present invention is of the type in which a prepackaged quantity of a medicament in an ampule is administered through a needle subcutaneously, most specifically by a plunger which is driven automatically to displace the medicament from the ampule through the needle and also serves to displace the needle from a retracted position in the instrument into the skin of the user.

BACKGROUND OF THE INVENTION

In many cases it is important that medicaments be administratable by an unskilled individual such as the patient himself by injection. For this reason so-called automatic syringes have been developed which, upon positioning against the skin, can be triggered so that the needle is automatically driven into the skin and medicament contained in the instrument is driven through the needle into the subcutaneous tissues.

Such syringes are desirable for patients suffering from allergies, various cardiovascular disorders and certain types of diabetes which may require immediate application of the injectable medicament so that there is no time for the patient to reach a skilled medical practitioner.

Probably the most significant of these disorders from the point of view of immediacy, is anaphylactic shock which can require an injection of epinephrine (adrenaline) without delay.

It is known to provide an automatic syringe which comprises a cylindrical barrel adapted to receive an ampule containing the medicament to be administered and which can be formed from a synthetic resin material and provided at its end turned toward the patient, with a fitting enabling a needle to be attached thereto so that the body of the ampule constitutes, simultaneously the carrier of the needle and the guide or support structure therefor.

In addition to the ampule, the barrel can be provided with a plunger which can be spring biased so as to drive the needle into the skin and expel the medicament from the ampule through the needle, a device for holding the plunger against the action of the spring until release is desired and a safety mechanism to prevent undesired discharge of the contents of the ampule.

In practice, the system in which the ampule body of molded synthetic resin constitutes the support for the needle and defines the wall of the container for the medicament has proved to be disadvantageous at least for certain medicaments such as adrenaline.

OBJECTS OF THE INVENTION

It is, therefore, the principal object of the present invention to provide an improved syringe of the type previously described, i.e. wherein the medicament is prepackaged in an ampule, whereby the drawbacks of earlier devices are avoided.

A more specific object of this invention is to provide a syringe for the purposes described, especially an automatic syringe, which has increased versatility with respect to the medicaments which can be used therein.

It is yet another object of my present invention to provide a syringe capable of use by an unskilled individual which is nevertheless reliable and effective for medicaments of all types

SUMMARY OF THE INVENTION

These objects and others which will become apparent hereinafter are attained, in accordance with the invention, by providing the automatic syringe of the class described with an ampule consisting of a body of one material and a device for maintaining the position of the needle and blocking discharge therethrough in the retracted position, i.e. before use, of a material different from that constituting the body of the ampule.

It is thus possible, in accordance with the invention, to form the body of the ampule of glass, a material which is compatible with practically all liquid medicaments, while the obturator and positioning device can be composed of another material and can have a significantly more limited contact with the medicament than the glass body. This device can be composed of a synthetic resin masterial.

By providing a body of the ampule of one material and a support and obturating device for the ampule of another material, therefore, I am able to greatly increase the field of application of the automatic syringe of the present invention.

According to a feature of the invention, the cylindrical glass body of the ampule can receive a piston of synthetic resin at its end remote from the needle, this piston being engageable by the spring-loaded plunger in the manner described.

In one embodiment, the spring-loaded end of the body can have an inwardly extending annular flange which engages in an outwardly open circumferential groove in a synthetic resin disk or grommet which can be pierced by the rear end of the needle as the needle is engaged by a device at the end of the barrel of the syringe, thereby enabling discharge of the medicament through the needle.

Alternatively, the cylindrical body of the ampule may extend to the end of the syringe which is applied to the skin of the user and the liquid medicament is retained between the piston and a sealing disk which is axially shiftable in the body and forms a guide for the rear end of the needle. In this case, a slug of the liquid medicament between the piston and the disk is advanced with the needle until the needle is captured at the end of the barrel and at this point the rear end of the needle penetrates the disk to allow discharge of the medicament by further advance of the piston, the disk being then immobilized.

When the ampule is sealed to the needle and communicates with the interior thereof in another embodiment of the invention, the leading end of the needle can be engaged by a seal at the extremity of the barrel which is applied to the skin of the user. Of course, it is also possible to seal the needle to the ampule but retain the liquid medicament as a slug within the ampule spaced from the needle between the piston and a disk which, by the force of the plunger, is released after the ampule has reached the limit of its travel to permit the liquid to be discharged through the needle.

In all cases, the end of the syringe which is applied to the skin of the user should be closed by a membrane or web which can be pierced by the needle, thereby insuring complete sterility of the needle until it enters the skin.

BRIEF DESCRIPTION OF THE DRAWING

The above and other objects, features and advantages of the present invention will become more readily apparent from the following description, reference being made to the accompanying drawing in which:

FIG. 5 is an axial section to a larger scale of the ampule of the syringe of FIGS. 1–4;

FIGS. 6 and 7 are axial sections through a portion of the barrel of another automatic syringe illustrating the ampule in its ready position and in its injection position respectively;

FIGS. 8 and 9 are longitudinal sectional views illustrating a third embodiment of the ampule of the invention showing the associated end of the syringe with which the ampule is used, also respectively in the storage state and the activated state;

SPECIFIC DESCRIPTION

Figure 1:
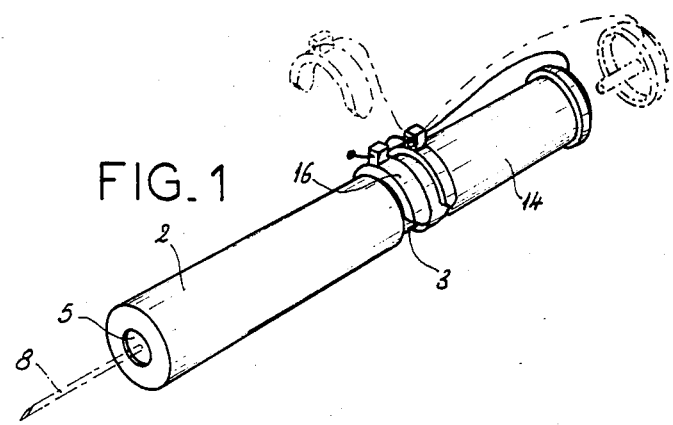
FIG. 1 is an automatic perspective view of an automatic syringe which can embody an ampule of the present invention showing the safety device and firing device removed and the needle extending in dot-dash lines.

In FIGS. 1–4 of the drawing 1 have shown all of the elements of a syringe according to the invention. In the remaining Figures, I have illustrated only the ampule or the combination of the ampule with the end of the barrel of the syringe to be applied to the skin of the user. It will be understood, therefore, that the plunger, trigger and safety assembly of FIGS. 1–4 is applicable to the ampules and barrel assemblies of the other Figures as well.

As can be seen from FIGS. 1–4, the syringe basically comprises a cylindrical housing in which the barrel consists of two parts, namely a front part 2 and a rear part 3 interconnected by a screw thread 4. Separation of the two barrel parts 2 and 3 at the screw thread permits an ampule to be inserted into the barrel part 2.

The barrel part 2 is provided at its end wall with an opening 2' closed by an elastomeric disk 5 which forms a web or membrane which can be pierced by a needle.

The barrel part 2 thus receives an ampule 6 containing a liquid medicament 7 and carrying at its forward end, the needle 8 in a manner which will be described in greater detail in connection with FIG. 5.

The other end of the ampule is closed by a sliding piston 9.

Figure 2:
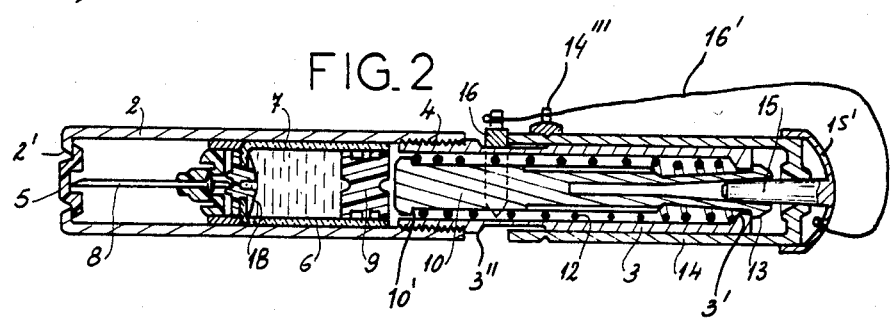
FIG. 2 is an axial section through the syringe in its secured state.

In the rest or storage position shown in FIG. 2, the ampule 6 and the needle 8 are disposed fully within the barrel part 2 and hence the needle 8 is not exposed to the environment and is maintained in a sterile condition.

The rear barrel part 3 contains a plunger 10 which is biased to the left by a compression spring 12. More particularly the plunger 10 has shoulder 10' against which one end of the spring 12 is seated, the other end of the spring bearing against an inwardly extending flange 3' of the barrel part 3. The spring is held in a prestressed state by the engagement of hooks 13 of the plunger 10 over the flange 3'.

Surrounding the barrel part 3 is an axially shiftable actuating sleeve 14 which has a cam formation 14' at its rear end, this cam formation being engageable with the hooks as the sleeve is driven to the left to press the hooks inwardly so they are liberated from the flange 3' and the spring 12 can displace the plunger to the left.

To prevent the displacement of the sleeve 14 in this manner when such displacement is undesired, a C-shaped clip 16 is releasably fitted between the end of the sleeve 14 and a shoulder 3" of the barrel part 3 around this barrel part. An additional safety device is formed by a cap 15' which engages over the end of the sleeve 14 and carries a pin which passes through the opening 14" in the end of this sleeve and wedges the hooks 13 outwardly.

The tapered pin 15 is readily retracted upon removal of the cap and the clip 16 can be removed as shown in dot-dash lines to enable the sleeve 14 to be displaced and to release the percussion plunger 10. The cap and the clip are held together by a lanyard 16' passing through an eye 14''' affixed to the sleeve to prevent loss of the cap and the clip.

Figure 3:
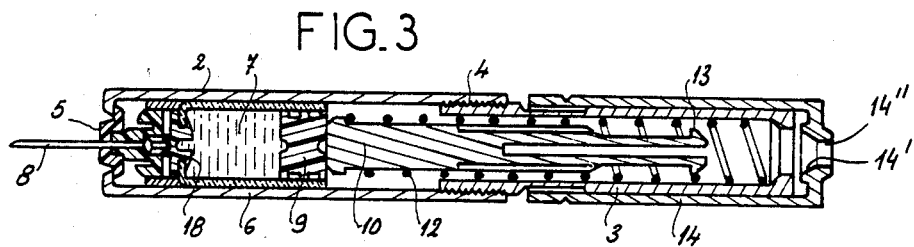
FIG. 3 is an axial section of the syringe after firing so that the needle has emerged but before the displacement of the liquid has commenced.
Figure 4:
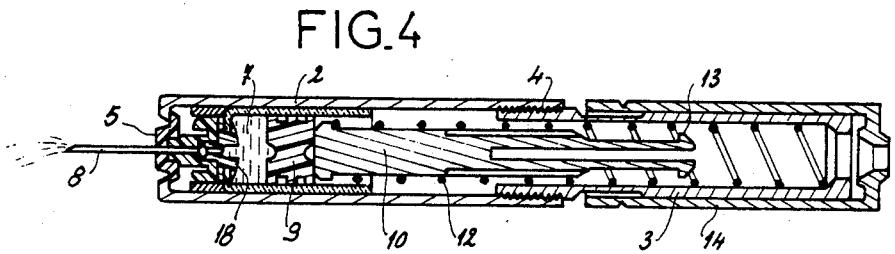
FIG. 4 is another longitudinal section showing the displacement of the liquid.

Once the cap and the clip have been removed, the sleeve 14 is displaced to the left, thereby camming the hooks 13 inwardly and aligning the spring 12 to drive the plunger 10 to the left and entrain the ampule 6 in this direction so that the needle 8 will pierce the disk 5 (FIG. 3). The ampule is thereby immobilized against the disk 5 and, upon piercing of the seal of the ampule in a manner which will be described in connection with FIG. 5, the displacement of the plunger 10 continues to force the piston 9 to the left and expel the medicament 7 through the needle.

Referring now to FIG. 5 it can be seen that the ampule 6 comprises a body 6' of glass, this cylindrical body having an inwardly turned flange 6" surrounding an opening 17. The cylindrical body 6' is freely open at its opposite end and receives the piston 9 which is composed of a silicone elastomer.

The opening 17 is blocked by a double-lip grommet 18 or dish of a somewhat yieldable elastomeric or synthetic resin material and which has an H cross section defined by an annular outwardly open groove 18' snugly receiving the flange 17.

This grommet thus has a core which fits into the opening 17, one annular lip 19 bearing on the inner face of the flange and an annular outer lip 20 bearing upon the outer face of the flange.

The outer lip 20 engages in and carries a cylindrical sleeve 22 which can be composed, for example of polypropylene which, in turn, engages a needle carrier 23 of polyethylene.

The core 24 of the grommet 18 is of extremely small wall thickness to form a web which can be perforated by the sharpened rear end 8' of the needle 8 lodged in the holder 23. Additional guidance can be provided by a cylindrical boss 24 of the grommet which can engage in a cylindrical recess 23' in the needle holder. It is thus apparent that once the needle carrier 23 engages the wall formed by disk 5 (FIG. 3) the needle 8 and the needle carrier are held against further displacement to the left and the needle carrier, in turn, forms a stop for the grommet 18 and thereby prevents further displacement of the ampule 6 to the left. Since the needle is immobilized as the grommet 18 is forced against the support 23, the point 18' penetrates the web 24 and establishes communication with the interior of the ampule as the plunger 10 drives the ampule and the piston 9 to the left.

In FIGS. 6 and 7 the body of the ampule is formed by a simple cylindrical glass sleeve 25 which need not be displaced in the barrel 2 of the syringe. This cylindrical body 25 has a length substantially greater than that required for the slug 7 of liquid medicament which is to be administered.

The cylindrical body 25 is closed at its rear end by a piston 9 in the manner previously described and at its front end by a disk 26 which is juxtaposed with and abuts the disk 5 previously mentioned. The disk 26 serves to guide the needle 8 during its displacement to the left as a comparison of FIGS. 6 and 7 will show.

The slug of liquid is defined between the piston 9 and a disk 27 which in turn is slidable within the glass body 25 and has a web 30 which is thin and can be pierced by the sharpened rear end 8' of the needle 8. The disk 27, which forms a plunger, has a cylindrical guide recess 28 which receives the needle carrier 29.

Consequently, when the plunger 10 is driven to the left, the assembly 27, 71, 9 is displaced to the left as a unit because of the incompressibility of the liquid, thereby driving the needle 8 through the disk 5 and at the same time causing the web 30 to be pierced by the point 8' and establishing communication with the body of liquid. The needle carrier 29 has a male formation 29' which engages in the recess 26' of the disk 26 and is thus immobilized while the disk 27 continues to move to the left for the piercing action and is ultimately immobilized. Continued displacement of the piston 9 to the left drives the liquid through the needle into the skin.

In all cases, the syringe is positioned so that the end formed with the disk 5 is pressed against the skin at the point at which the injection is to occur. For convenience and simplicity the piston 9 can have the same configuration as the disk 27.

Figure 9:
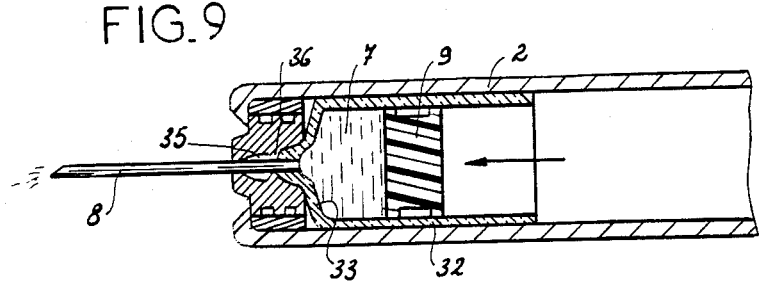

In the embodiment illustrated in FIGS. 8 and 9, the ampule 32 has a cylindrical configuration and is closed at its rear end by a piston 9 in the manner described while its front end 33 is drawn into a glass/metal seal with the needle 8. In this case the obturator for the needle is formed by a disk 34 which replaces the disks 26 and 5 and has a seal 36 engaging the periphery of the needle, a cavity 35 in which the leading end of the needle is lodged, and a web 34' which is pierced by the needle.

The ampule is thus sealed against the exterior in spite or the fact that the liquid 7 is continuously in connection with the needle.

As the ampule is driven to the left (FIG. 9) by the plunger 10, the web 34' is pierced and the displacement is continued until the leading end of the ampule lodges in the disk 34 whereupon continued displacement of the plunger can drive the piston 9 to the left to expel the liquid through the needle.

Figure 10:
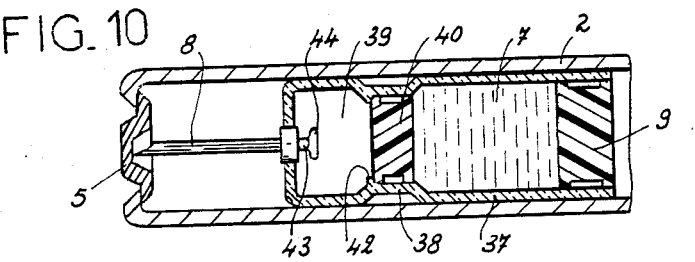
FIGS. 10 and 11 are axial sections of a fourth embodiment of the ampule and the associated end of the syringe, also in the storage state and the activated state respectively.
Figure 11:
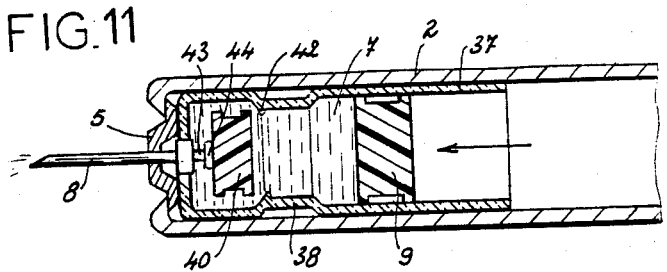

FIGS. 10 and 11 illustrate the embodiment in which the needle 8 is sealed to the end of the glass ampule 37 but has a lateral opening 43 behind a head 44 in connection with a chamber 39. The chamber 39 is defined by a constriction 38 which has a slight shoulder 42 engaging a sealing disk or plug 40 which delimits the liquid slug 7 which is also bounded by the piston 9. The plug 40 is yieldable so that as the slug of liquid is driven to the left, it is displaced past the shoulder 42 (see FIG. 11) in this embodiment. Moreover, the barrel 2 of the syringe is closed by a disk 5 which is pierced by the needle as the ampule is first forced to the left. Only upon engagement of the end of the ampule with the disk 5 (FIG. 11) is the force applied by the plunger 10 sufficient to displace the slug of liquid to the left within the ampule, free the plug 40 and enable the liquid to be displaced through the needle 8. The head 44 forms an abutment preventing the plug 40 from blocking the opening 43.

Figure 12:
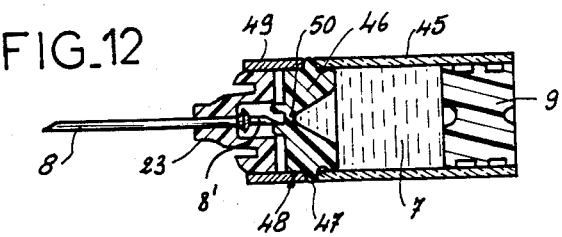
FIG. 12 is a longitudinal section through an ampule which represents a modification of the embodiment shown in FIG. 5.

Finally in FIG. 12 I show a modification of the ampule of FIG. 5 in which the glass ampule body is of simple cylindrical section, i.e. is of constant cross section. One end is provided with the piston 9 while the other end is formed with a plug 46 which has a male portion engaging in the cylindrical body 45 and a further cylindrical portion 48 engaging in the sleeve 49, these cylindrical portions being separated by a peripheral shoulder 47 which abuts both the sleeve 49 and the cylindrical body 45. The sleeve 49 surrounds and guides the needle carrier 23 in the manner described. A thin wall portion 50 of the plug 46 can be pierced by the point 8' of the needle as previously described.

I claim:

1. A medical syringe comprising:
   a barrel having one end adapted to be applied against the skin of a user for injection;
   a plunger mounted on an opposite end of said barrel and spring biased so as to be driven toward said one end upon release;
   an ampule containing a liquid medicament to be injected beneath the skin of said user, said ampule being slidably received in said barrel and movable toward said one end thereof, said ampule including:
   a cylindrical glass body;
   a piston received in one end of said body proximal to said plunger and slidable in said body,
   a disk fixed in an opposite end of said body proximal to said one end of said barrel, said piston and said disk receiving between them an injection dose of said liquid medicament, said disk having a central thin-walled portion adapted to be perforated and a shoulder extending toward said one end of said barrel of a diameter less than that of said body,
   a sleeve fixed on said shoulder of said disk,
   a needle support slidably received in said sleeve and having a central boss aligned with said thin-walled portion, and
   a hypodermic needle received in said boss and having a sharpened first end juxtaposed with but spaced from said thin-walled portion and a second end reaching toward said one end of said barrel; and
   an obturator closing said one end of said barrel and adapted to be pierced by said needle when said ampule is driven toweard said one end of said barrel by engagement of said plunger with said piston whereby said first end is then caused to pierce said thin-walled portion so that further displacement of said piston in said body by said plunger drives said medicament beneath the skin of the user.

2. The medical syringe defined in claim 1 wherein said disk is formed with a cylindrical tubular boss aligned with said central thin-walled portion and adapted to receive said one end of said needle, said needle support being formed with a cylindrical recess adapted to receive said boss.

* * * * *